United States Patent [19]

Farris et al.

[11] Patent Number: 4,673,355

[45] Date of Patent: Jun. 16, 1987

[54] SOLID CALCIUM PHOSPHATE MATERIALS

[76] Inventors: Edward T. Farris, 4715 Greenville Ave., Dallas, Tex. 75206; John J. Barsa, 60 Haven Ave., New York, N.Y. 10032; Richard J. Lagow, 6204 Shadow Mountain Dr., Austin, Tex. 78731; Paul J. Capano, 1730 E. Oltorf, Austin, Tex. 78741

[21] Appl. No.: 764,515

[22] Filed: Aug. 9, 1985

Related U.S. Application Data

[63] Continuation of Ser. No. 436,615, Oct. 25, 1985, abandoned.

[51] Int. Cl.$^4$ .................. C08L 93/04; C09K 3/00; C01B 25/32; A61F 1/24
[52] U.S. Cl. .................. 433/218; 433/222.1; 433/223; 106/35; 423/311
[58] Field of Search .................. 106/35; 3/1.9; 128/92 C, 92 G; 433/201, 202, 218, 228.1, 222, 223; 423/311

[56] References Cited

U.S. PATENT DOCUMENTS

| | | | |
|---|---|---|---|
| 2,508,816 | 5/1950 | De Ment | 524/10 |
| 3,379,541 | 4/1968 | Tuvell | 106/38.27 |
| 3,913,229 | 10/1975 | Driskill et al. | 433/228.1 |
| 3,929,971 | 12/1975 | Roy | 423/308 |
| 4,046,858 | 9/1978 | Barsa et al. | 423/305 |
| 4,048,300 | 9/1977 | Tomlinson et al. | 424/52 |
| 4,097,935 | 7/1978 | Jarcho | 623/16 |
| 4,113,500 | 9/1978 | Ebihara et al. | 501/1 |
| 4,131,597 | 12/1978 | Bluethgen et al. | 523/114 |
| 4,135,935 | 1/1979 | Pfeil et al. | 106/35 |
| 4,149,893 | 4/1979 | Aoki et al. | 106/35 |
| 4,207,306 | 6/1980 | Jarcho | 423/633 |
| 4,222,128 | 9/1980 | Tomonaga et al. | 623/16 |
| 4,223,412 | 9/1980 | Aoyagi et al. | 623/16 |
| 4,224,072 | 9/1980 | Stewart | 106/35 |
| 4,230,455 | 10/1980 | Hidaka et al. | 23/313 AS |
| 4,235,633 | 11/1980 | Tomioka et al. | 106/35 |
| 4,274,879 | 6/1981 | Irvine | 501/142 |
| 4,308,064 | 12/1981 | Takami et al. | 501/135 |
| 4,324,772 | 4/1982 | Conn et al. | 423/309 |
| 4,330,514 | 5/1982 | Nagai et al. | 423/309 |
| 4,497,075 | 2/1985 | Niwa et al. | 423/311 X |

OTHER PUBLICATIONS

R. H. Stern et al., *Optics and Laser Technology*, p. 22, Feb. 1975.

*Primary Examiner*—Nancy A. Swisher
*Attorney, Agent, or Firm*—Hamilton, Brook, Smith and Reynolds

[57] ABSTRACT

This invention relates to the formation of a new solid material composed of calcium phosphates and to the reaction method for producing this material. The solid calcium phosphate material is created by chemically reacting calcium ion sources with phosphate ion sources in a molten state and cooling the reaction mixture to room temperature producing the solid material. Depending upon the ratio of components and the parameters of the heating reaction, the resulting material may be a smooth, non-porous material with exceptional hardness, or it may be a porous material. Both types of material can be shaped into desired configurations, such as artificial teeth.

31 Claims, No Drawings

SOLID CALCIUM PHOSPHATE MATERIALS

This is a continuation of co-pending application Ser. No. 436,615 filed on Oct. 25, 1985.

TECHNICAL FIELD

This invention is in the fields of chemistry, surgery, skeletal repair, artificial bone, tooth repair, artificial crowns and teeth, surgical implants, ceramics and bioceramics.

BACKGROUND ART

Certain types of calcium phosphate materials are biologically important. For example, apatitic calcium phosphates, hereafter referred to as apatites, are the primary mineral constituent of bone and teeth. Described generally, bone and tooth minerals proceed through a sequence of phases of which the final mineral phase is an apatite similar to hydroxyapatite, see e.g., I. Zipkin, *Biological Mineralization* (Wiley, 1973). The basic chemical formula of hydroxyapatite (also spelled hydroxylapatite) is $Ca_{10}(PO_4)_6(OH)_2$. The actual composition of bone and tooth minerals can vary substantially from this formula. For example, commonly present in the various phases of the mineralized tissues of bones and teeth are calcium-deficient apatite species, carbonate species and various other apatitic species such as fluoroapatite.

Hydroxyapatite is held together primarily by ionic bonding; the calcium ions are divalent cations ($Ca^{++}$), the phosphate ions are trivalent anions ($PO_4^{---}$), and the hydroxyl ions are monovalent anions ($OH^-$).

Hydroxyapatite and other forms of calcium phosphate have several advantages when used in repairing bones and tooth enamel. Since they have chemical compositions that are similar or identical to the mineral that exists naturally in bone and tooth enamel, calcium phosphates can be comparable to natural tooth and bone material with regard to numerous important parameters. Such parameters include thermal conductivity, thermal coefficient or expansion, hardness, strength, color, and insolubility in saliva and other acidic or basic solutions. Being thus comparable to natural tooth and bone material, calcium phosphates tend to be relatively biocompatible. As used herein, biocompatibility refers to any combination of characteristics which eliminate or minimize adverse reactions when a substance is implanted in the body. Such materials should not cause antigenic, pyogenic, pyrogenic, or inflammatory responses in the recipient. They should not cause galvanic currents, or be corroded, metabolize or dissolve into undesired substances.

There have been a substantial number of efforts to utilize various forms of apatite and other calcium phosphate materials in the repair and reconstruction of bone and tooth enamel. A number of patents and articles describe the use of hydroxyapatite obtained from marine coral and bone powder. See, e.g., U.S. Pat. Nos. 2,508,816 (bone powder) and 3,929,971 (marine coral).

Such materials often contain various other calcium phosphates, such as whitlockite and brushite.

Several other patents and articles describe synthetic apatite materials. See, e.g., U.S. Pat. Nos. 4,046,858 (Barsa et al, 1978); 4,274,879 (Irvine, 1981); 4,330,514 (Nagai et al, 1982); 4,324,772 (Conn et al, 1982); 4,048,300 (Tomlinson et al, 1977); 4,097,935 (Jarcho, 1978) 4,207,306 (Jarcho, 1980); 3,379,541 (Tuvell, 1968).

Several patents and articles describe methods of treating apatite materials in order to render them suitable for tooth implants and other prosthetic devices. Such techniques usually involve sintering or other methods of heating and compaction which convert powdery material into solid porous articles in various shapes. See, e.g., U.S. Pat. Nos. 4,308,064 (Takami et al, 1981); 4,113,500 (Ebihara et al, 1978); 4,222,128 (Tomonaga et al, 1980) 4,135,935 (Pfeil et al, 1979); 4,149,893 (Aoki et al, 1979); 3,913,229 (Driskill et al, 1975).

Several patents and articles describe the use of techniques such as laser radiation to bond apatite materials to tooth surfaces which have been drilled to remove tooth decay. See, e.g., U.S. Pat. No. 4,224,072 (Steward, 1980); R. H. Stern et al, *Optics and Laser Technology*, p. 22, February, 1975.

Several patents describe the use of particulate or compacted apatite in conjunction with various other compounds, such as fillers and cements. See, e.g., U.S. Pat. Nos. 4,230,455 (Hidaka et al, 1980); 4,223,412 (Aoyagi et al, 1980); 4,131,597 (Bluethgen et al, 1978).

The materials and methods cited above are likely to perform with varying degrees of success when used to promote the healing or restoration of bones and teeth. However, a need exists for continuing improvements in materials and techniques used to promote the regeneration of repair of bones or teeth.

DISCLOSURE OF THE INVENTION

This invention relates to the formation of a new solid material compound of calcium phosphates and to the reaction method for producing this material.

The solid calcium phosphate material is created by chemically reacting calcium ion sources with phosphate ion sources. Some suitable sources of calcium ions include apatitic calcium phosphates, such as crystalling hydroxyapatite, non-apatitic calcium phosphates, calcium hydroxide, calcium carbonate, calcium salts, calcium oxide, calcium halides and calcium metal. Some suitable sources of phosphate ions include orthophosphoric acids, pyrophosphoric acids, condensed phosphates, phosphates of non-metal cations and metal phosphates.

In one embodiment the various calcium and phosphate ion sources at room temperature are mixed, heated to a molten state, allowed to react, then cooled to generate the product material. In an alternate embodiment the various calcium and phosphate ion sources are heated separately to their molten states, mixed together already at the reaction temperature, allowed to react, and then cooled to generate the product material. Other alternate embodiments include heating to a molten state any one or combination mixture of the various calcium and phosphate ion sources subsequently adding other molten or solid calcium and phosphate sources, to it at the reaction temperature, allowing the mixture to react, then cooling to generate the product. The resulting product is a solid, hard material.

In addition other chemical substances and ion sources which may be especially useful and desirable because of their chemical, physical and/or biological properties or for their clinical importance, may be added to the unheated calcium and phosphate ion mixture or to the molten reaction mixture in a molten or solid form to be incorporated into the composition of solid product material. These chemical substances may also be attached to the surface of the solid product. This can be accomplished utilizing the strong adhesive property of the reaction mixture during the cooling step of the reaction process. In one embodiment, the various calcium and phosphate ion sources are mixed, heated to a molten state, allowed to react. At a temperature nearly solidifying the product material the near solid is contacted with a layer of some useful and desirable chemical substances. Then the cooling process is completed and the solid product material is removed. The product material is a hard, solid with a layer of the useful substance firmly attached. One such useful material for example could be an apatitic calcium phosphate such as hydroxyapatite which is known to have the property of enhancing bone regeneration and bone growth. Other useful substances include non-apatitic calcium phosphates and metal ions.

Depending upon the ratio of components and the parameters of the heating reaction, the resulting solid calcium phosphate material may be created in a smooth, non-porous form, or in a porous form. Each type of material has certain advantages; for example, the non-porous form is exceptionally hard, yet the porous form has a much larger surface area. Still both are strong solids with exceptional resistance to most solvents, e.g., acids, alkaline, acetone, alcohols, water, organics.

The solid calcium phosphate material of this invention can be molded, machined, or otherwise made into any desired shape, such as the shapes of teeth, tooth crowns, bones, etc. All types of the material are believed to have a high degree of biocompatibility, a high degree of cohesiveness to natural bone and tooth enamel, a thermal conductivity and a thermal coefficient of expansion which resemble natural hard tissue, and other properties which render them useful for the repair or replacement of bones and teeth.

BEST MODE OF CARRYING OUT THE INVENTION

In one preferred embodiment of this invention, the solid calcium phosphate material is produced by taking a mixture of orthophosphoric acid and powdered hydroxyapatite and heating it to a molten state to let react. Upon completion of the reaction, mixture is cooled to room temperature and the solid product is removed from its reaction vessel. Concentrated acid is preferred. Water is an undesirable and interferring substance particularly to the early stages of the reaction. Powdered hydroxyapatite may be purchased commercially or synthesized by a variety of methods, several of which are cited above.

For convenience, the following shorthand nomenclature will be used herein. An initial (unheated) calcium phosphate mixture will be referred to as $CPM_i$.

The calcium to phosphorous molar ratio (Ca/P) of apatite materials with the formula $Ca_{10}(PO_4)_6(X)_{1,2}$, where X is any monovalent or divalent anion other than one containing phosphorus, is 10/6 or 1.67. In this invention, a source of phosphate ions is added to a source of calcium ions. The Applicants have experimented with a wide range of initial Ca/P molar ratios (i.e., the "initial" ratio refers to the Ca/P ratio of the $CPM_i$ components before they are heated). Many favorable effects have been discovered controllable by altering the initial Ca/P molar ratio along with altering several other reaction conditions.

It has been discovered that if an initial Ca/P molar ratio of 0.24 is used, $CPM_i$ comprises a viscous white paste. If heated to 1000° C., the material reacts in a molten phase, and when cooled the product material removed will be a non-porous solid.

If $CPM_i$ with an initial Ca/P molar ratio of 0.29 is reacted at less than 1000° C. it will form a porous white solid following cooling. However, if reaction is continued and the temperature is increased to about 1100° C. for five hours, the product material removed after cooling will be non-porous solid.

$CPM_i$ with an initial Ca/P molar ratio of 0.62 or higher comprises a white powder rather than a viscous paste. If reacted at 1100° C. for five hours, the resulting material becomes a highly porous, coralline solid. The high level of porosity tends to decrease the overall strength of the material, although it is believed that the strength of a microscopic piece of this material is roughly equal to the strength of a piece of non-porous solid calcium phosphate material of the same size. If $CPM_i$ with a Ca/P molar ratio of 0.62 is heated for longer than five hours, the porosity decreases significantly; this provides a method of controlling the porosity of solid calcium phosphate material. If $CPM_i$ with a Ca/P molar ratio of 0.62 is heated for a sufficiently long period, such as about nine days, the resulting solid calcium phosphate material is a non-porous solid.

Controlling the Ca/P molar ratio and several reaction conditions has therefore a controlling effect on physical and chemical properties of the solid calcium phosphate material. For mixtures which are heated to a given temperature for a given period of time, an increase in Ca/P molar ratio of a $CPM_i$ mixture tends to increase the porosity of the resulting solid calcium phosphate material. At Ca/P molar ratios of 1.15 or more, materials heated to 1100° C. for five hours tend to be brittle. At Ca/P molar ratio of 1.34, materials heated to 1100° C. tend to remain in powdered form.

A variety of methods can be used to heat calcium phosphate mixtures. An electric furnace with a resistance coil was utilized by the Applicants. Radio frequency heating, laser radiation, microwave radiation, and other forms of heating may be suitable, as may be determined by those skilled in the art. As used herein, the term "furnace" is used to refer to any device which is capable of heating a mixture of calcium and phosphate ions to a molten state where the reactants may react. A furnace may be equipped with various devices to enhance the heating reaction. For example, the furnace chamber may be filled with an atmosphere of inert gas. The chamber may be equipped with temperature sensors, or mechanical devices to facilitate the manipulation of molten liquids.

In one preferred embodiment of this invention, the heating and cooling processes can be performed relatively quickly. For example, a furnace may be heated to a desired temperature, such as 1100° C. A crucible which holds a calcium phosphate mixture at room temperature can be inserted into the furnace, heated for the desired period of time, and removed from the furnace to cool to room temperature. This eliminates the need for gradual or controlled heating or cooling of the furnace. It allows for rapid creation of solid calcium phosphate material, and for efficient utilization of a furnace.

If desired, cooling may be accelerated or controlled by various techniques, such as contacting the crucible with a liquid or cooled gas. The cooling rate may alter the crystal structure and mechanical and other properties of the final product. Solid calcium phosphate materials cooled at certain rates may be preferable for specific uses, as may be determined by those skilled in the art.

In another preferred embodiment of this invention, $CPM_i$ can be heated to below its molten phase, for example 900° C. This will drive off all undesirable materials such as water. The resulting material is still a powder which can be stored indefinitely. This powdered material may subsequently be heated and allowed to react in the molten phase as described before to form the solid product upon cooling. Reaction time is reduced quite significantly.

It is possible to create solid calcium phosphate material using crucibles made of various substances, including metal, quartz, or cement mixtures. It is possible to utilize the crucible as a mold with a desired shape, or to pour molten material from a crucible into a mold. It is believed that cold mold techniques may provide certain advantages, such as reducing the adherence of the calcium phosphate material to the mold. Machining techniques also may be utilized to adjust and perfect the shape and size of the molded solid product.

The materials of this invention are relatively insoluble to all biological fluids, such as saliva, lactic acid, formic acid, etc.

The materials of this invention may comprise a variety of crystalline and possibly amorphous substances, depending upon the specific ratio of reagents used and the reaction parameters. Various types of analyses have indicated that solid calcium phosphate materials include apatite calcium phosphates, pyrophates, metaphosphate and orthophosphate species.

For certain uses the non-porous and porous calcium phosphate materials have several significant advantages compared to the other solidified calcium phospate materials such as sintered hydroxyapatite. Those advantages include the following. The non-porous product generated by the Applicants procedure is substantially harder than the porous, sintered apatite materials. Therefore, it is a preferable material for uses which include high stress, such as a hard tissue restorative, e.g., tooth or bone. Also, the non-porous materials lower surface area to volume ratio implies that the non-porous product is more resistant to various types of fluids or solvents than the porous sintered materials. In addition, the ability to control porosity, even in only specific areas of the generated product, allows a material to be produced which can be partially non-porous and partially porous. This advantage can be significant in the fields of bone regeneration, surgical implants and bioceramics.

This invention is more specifically illustrated by the following examples.

EXAMPLES

Example 1

Seven parts by weight of 85 percent orthophosphoric acid ($H_3PO_4$) are added to four parts by weight of calcium metal turnings in a high temperature crucible. The mixture reacts exothermically at room temperature to produce a white, amorphous precipitate. Heat is added progressively to the precipitate by applying the flame from a gas torch to the high temperature crucible. As heat is added, the white precipitate looses viscosity and begins to boil at about 100° C. As more heat is added the boiling precipitate becomes clearer and more viscous. As the temperature reaches about 450° C., the boiling ceases. Heating is continued with the temperature steadily increasing to about 1000° C. The clear precipitate material then initiates decomposition and forms a white, amorphous material which at this temperature is dripped onto a molybdenum sheet to cool to white hard solids in the shape of small beads.

Quantitative chemical analysis of the beads shows that they contain 0.02 percent hydrogen; 25.10 percent calcium; and 27.83 percent phosphorus.

Infrared analysis and X-ray powder pattern diffraction analysis made on the solid, white product, using a Perkin Elmer 467 Grating Infrared Spectrometer and a Phillips Electronic Instruments water-cooled X-ray diffraction unit respectively, showed a mixture of calcium phosphates as the chemical composition.

The material's hardness was shown to be similar to that of natural tooth enamel.

Example 2

10 grams of powdered hydroxyapatite (sold by Mallinkrodt under the name "Calcium Phosphate Tribasic $Ca_{10}(PO_4)_6(OH)_2$, Analytical Reagant") was mixed thoroughly with 34 grams of 85 percent orthophosphoric acid. The reactants reacted exothermically and formed a very viscous, white paste. The mixture was then heated in an electric furnace using a high temperature crucible as a vessel for the reaction. A maximum reaction temperature of 1150° C. for a period of seven hours was used. Subsequently the heated material was removed from the furnace and rapidly cooled to room temperature in air. The white, non-porous product had a hardness of approximately 5.2 (Mohl scale) and a specific gravity of approximately 3.0.

Example 3

10 grams of powdered hydroxyapatite (Mallinkrodt) was mixed with 8.5 grams of 85 percent orthophosphoric acid. The materials reacted exothermically to become a white powder. The powder was then heated to 900° C. in an electric furnace for four hours to produce a white powder. This powder was ground up finely for better storage and stored on the shelf over an indefinite period of time unchanged in chemical or physical composition. Percent weight loss from the initial mixture to the powdered product was approximately 20 percent.

Example 4

The stored powdered material, the same as that produced in Example 3, was placed in a high temperature container the interior of which was shaped in the form of a dental implant. The powdered reactant was heated in an electric furnace at 1100° C. and allowed to react for 1½ hours. The product material was removed and let cool to room temperature in air. The generated product material was a hard, non-porous, white solid. The percent weight loss from the initial stored powder material, as produced in Example 3, to the final solid product was 0 percent.

Example 5

The stored powdered material, the same as produced in Example 3, was placed in a high temperature mold shaped into the form of the tibia of a rat. The material was heated at 1100° C. for 1½ hours, removed and let cool to room temperature. The product generated was a hard, white, non-porous solid molded into the form of a rat tibia.

Example 6

The stored powdered material, the same as produced in Example 3, was placed in a high temperature mold shaped into the form of a human skull cap. On the inner surface of the mold a layer of powdered hydroxyapatite (Mallinkrodt) was placed before the powdered reactant was added. The material was heated to 1010° C. (just above the temperature needed to make the mixture molten) for 1½ hours, removed and let cool to room temperature. The product generated was a hard, white, non-porous solid molded into the form of a human skull cap. On the lower surface of the skull cap was firmly attached a layer of hydroxyapatite. Hydroxyapatite is known to enhance bone regeneration and bone growth. Some machining was performed to perfect the shape and size of the artificial skull cap.

Example 7

The stored powdered material, the same as produced in Example 3, was placed in a high temperature container. The material was heated at 1100° C. for 1½ hours. Subsequently a third substance was added to the molten solution, powdered hydroxyapatite (Mallinkrodt). Following the addition of the powder, reaction mixture was removed and let cool to room temperature. The product generated was a hard, non-porous, white solid whose composition under analysis displayed a large amount of apatitic calcium phosphate.

Example 8

One part by weight of powdered hydroxyapatite was mixed with two parts by weight of 85 percent orthophosphoric acid. The mixture reacted exothermically, and subsequently was allowed to cool down. The resulting thin paste was placed into the cavity of a tooth and then given several 1-to-10 microsecond length, 5 megawatt, 0.5 cm. diameter pulses from a "Lumonica 201" carbon dioxide pulsed laser. The paste boiled rapidly. The final tooth structure showed that a small amount of the paste became firmly bonded to the tooth enamel, forming a hard white surface. The process was repeated, using 10–500 microsecond pulses at 45 watts. Less boiling occurred and substantial quantities of the paste became firmly bonded to the tooth enamel, forming a hard, shiney white surface.

We claim:

1. A method of producing a nonapatitic solid material containing calcium and phosphate, comprising the steps of:
   a. forming a reactant mixture of calcium ions and phosphate ions in phosphoric acid, the mixture having a calcium to phosphate ratio of about 0.1 to about 1.34;
   b. heating the mixture to a molten state of above about 750° C. at which the ions react; and
   c. cooling the reaction mixture thereby forming a nonapatitic solid calcium phosphate material.

2. A method of claim 1, further comprising the step of preheating the mixture to a temperature below the reaction temperature.

3. A method of claim 1, further comprising the step of incorporating into the mixture of calcium and phosphate ions, either before or during heating to the molten state, apatitic calcium phosphates or metal ions.

4. A solid calcium phosphate material prepared by the method of claim 3.

5. A method of claim 1, wherein the calcium ions are provided by any one or any combination of the sources of calcium ions selected from the group of materials consisting of apatitic calcium phosphates, non-apatitic calcium phosphates, calcium hydroxide, calcium oxide, calcium carbonate, calcium salts, calcium halide and calcium metal.

6. A method of claim 1, wherein the phosphate ions are provided by any one or any combination of the sources of phosphate ions selected from the group of materials consisting of orthophosphoric acid, pyrophoric acids, condensed phosphates, phosphate of non-metal cations and metal phosphates.

7. A method of claim 1, wherein the mixture is heated in an electric furnace.

8. A method of claim 1, wherein the mixture is heated by means of laser excitation, microwave radiation or radio frequency radiation.

9. A nonapatitic solid calcium phosphate material produced by the method of claim 1.

10. A method of producing a nonapatitic solid material containing calcium and phosphate, comprising the steps of:
    a. forming a mixture of hyroxyapatitde and phosphoric acid having a calcium to phosphorous molar ratio of about 0.1 to about 1.34;
    b. heating the mixture to a molten state of above about 750° C.; and
    c. cooling the mixture to produce a solid calcium phosphate material.

11. A solid calcium phosphate material produced by the method of claim 10.

12. A method of producing a non-apatitic, solid, porous material containing calcium and phosphate, comprising the steps of:
    a. forming a mixture of hydroxyapatitde and phosphoric acid having a calcium to phosphorus molar ratio of about 0.5 to about 1.34;
    b. heating the mixture to a molten state of above about 850° C.; and
    c. cooling the mixture to produce a solid, porous calcium phosphate material.

13. A method of claim 12, further comprising the step of preheating the mixture to a temperature below the molten state temperature.

14. A porous calcium phosphate material produced by the method of claim 12.

15. A method of claim 12, for producing a molded porous calcium phosphate material, further comprising the step of placing the mixture into a mold of a desired shape before the heating step.

16. A method of claim 12, wherein the mixture is heated in an electric furnace.

17. A method of claim 12, wherein the mixture is heated by means of laser excitation, microwave radiation or radiofrequency radiation.

18. A tooth restorative comprising a calcium phosphate material produced by the method of claim 12.

19. A surgical implant comprising a calcium phosphate material produced by the method of claim 12.

20. A nonapatitic, solid, essentially non-porous material containing calcium and phosphate, comprising the steps of:
    a. forming a mixture of hydroxyapatite and phosphoric acid having a calcium to phosphorous molar ratio of about 0.1 to about 0.5;
    b. heating the mixture to a molten state of above about 750° C.; and c. cooling the reaction product to form a solid, essentially nonporous calcium phosphate material.

21. A method of claim 20 wherein the mixture is heated to a temperature of about 900°–1100° C.

22. A method of claim 20 further comprising the step of preheating the mixture to a temperature below the molten state temperature.

23. A nonapatitic solid, essentially nonporous calcium phosphate material produced by the method of claim 20.

24. A method of claim 20, for producing a molded essentially nonporous calcium phosphate material, further comprising the step of placing the mixture into a mold of a desired shape before the heating step.

25. A method of claim 20, wherein the mixture is heated in an electric furnace.

26. A method of claim 20, wherein the mixture is heated by means of laser excitation, microwave radiation or radiofrequency radiation.

27. A method of claim 20, for forming a tooth restorative, further comprising the step of placing the mixture into a tooth defect before heating.

28. A method of claim 27, wherein the mixture is heated by means of laser excitation.

29. An artificial tooth crown comprising a crown-shaped piece of the nonapatitic solid, essentially nonporous calcium phosphate material produced by the method of claim 20.

30. A tooth restorative comprising a calcium phosphate material produced by the method of claim 20.

31. A surgical implant comprising a calcium phosphate material produced by the method of claim 20.

* * * * *